(12) United States Patent
Zhang

(10) Patent No.: US 9,964,481 B2
(45) Date of Patent: May 8, 2018

(54) METHOD AND SYSTEM FOR EXHAUST PARTICULATE MATTER SENSING

(71) Applicant: Ford Global Technologies, LLC, Dearborn, MI (US)

(72) Inventor: Xiaogang Zhang, Novi, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 186 days.

(21) Appl. No.: 14/845,683

(22) Filed: Sep. 4, 2015

(65) Prior Publication Data

US 2017/0067813 A1   Mar. 9, 2017

(51) Int. Cl.
| | |
|---|---|
| *G01N 15/06* | (2006.01) |
| *G01M 15/10* | (2006.01) |
| *F01N 11/00* | (2006.01) |
| *F02D 41/22* | (2006.01) |
| *F02D 41/14* | (2006.01) |
| *G01N 15/00* | (2006.01) |

(52) U.S. Cl.
CPC ......... *G01N 15/0656* (2013.01); *F01N 11/00* (2013.01); *F02D 41/1466* (2013.01); *F02D 41/1494* (2013.01); *F02D 41/1496* (2013.01); *F02D 41/22* (2013.01); *G01M 15/102* (2013.01); *G01N 15/0606* (2013.01); *F01N 2550/04* (2013.01); *F01N 2560/05* (2013.01); *F01N 2900/0422* (2013.01); *G01N 2015/0046* (2013.01); *Y02T 10/40* (2013.01); *Y02T 10/47* (2013.01)

(58) Field of Classification Search
CPC ............. B03C 2201/30; B03C 3/0175; G01N 15/0656; G01N 15/02; G01N 15/0606; G01N 2015/0046
See application file for complete search history.

(56) References Cited

U.S. PATENT DOCUMENTS

| | | | | |
|---|---|---|---|---|
| 4,228,128 | A * | 10/1980 | Esper | G01N 27/12 |
| | | | | 324/71.5 |
| 7,048,844 | B2 * | 5/2006 | Chen | G01N 27/419 |
| | | | | 204/426 |
| 7,543,477 | B2 | 6/2009 | Berger et al. | |
| 8,377,274 | B2 * | 2/2013 | Ohya | G01N 27/4075 |
| | | | | 204/421 |
| 8,823,401 | B2 | 9/2014 | Roth et al. | |
| 9,289,780 | B2 * | 3/2016 | Goodson | B01D 46/0032 |
| 2004/0117974 | A1 * | 6/2004 | Clyde | G01N 27/4075 |
| | | | | 29/592.1 |

(Continued)

*Primary Examiner* — David A Rogers
(74) *Attorney, Agent, or Firm* — Julia Voutyras; McCoy Russell LLP

(57) ABSTRACT

Methods and systems are provided sensing particulate matter by a particulate matter (PM) sensor positioned downstream of a diesel particulate filter (DPF) in an exhaust system, where the PM sensor may include plurality of individual electrode pairs coupled to plurality of voltage sources and further to plurality of measurement devices. In one example, a method may include determining a total PM sensor current by summing current generated across the plurality of electrode pairs by determining the sum total of the current generated across the individual electrode pairs. In this way, the PM sensor may detect PMs in the exhaust more accurately, and not be affected by large particulates depositing on the electrodes.

12 Claims, 7 Drawing Sheets

(56) References Cited

U.S. PATENT DOCUMENTS

| | | | |
|---|---|---|---|
| 2005/0050968 A1* | 3/2005 | Trenholm | G01N 15/02 |
| | | | 73/865.5 |
| 2006/0090540 A1* | 5/2006 | Gardiner | F02D 41/1466 |
| | | | 73/23.33 |
| 2007/0045114 A1* | 3/2007 | Wang | C03C 8/14 |
| | | | 204/431 |
| 2008/0190173 A1 | 8/2008 | Wienand et al. | |
| 2011/0246089 A1* | 10/2011 | Barrett | G01N 15/0266 |
| | | | 702/24 |
| 2012/0008143 A1* | 1/2012 | Ihlefeld | G01N 15/0205 |
| | | | 356/335 |
| 2013/0255482 A1* | 10/2013 | Goodson | B01D 46/0032 |
| | | | 95/3 |
| 2013/0257460 A1* | 10/2013 | Roth | G01N 15/0656 |
| | | | 324/699 |
| 2016/0175851 A1* | 6/2016 | Goodson | B01D 46/0032 |
| | | | 95/3 |

\* cited by examiner

METHOD AND SYSTEM FOR EXHAUST PARTICULATE MATTER SENSING

FIELD

The present description relates generally to the design and use of resistive-type particle matter (PM) sensors in an exhaust gas flow.

BACKGROUND/SUMMARY

Diesel combustion exhaust is a regulated emission. Diesel particulate matter (PM), is the particulate component of diesel exhaust, which includes diesel soot and aerosols such as ash particulates, metallic abrasion particles, sulfates, and silicates. When released into the atmosphere, PMs can take the form of individual particles or chain aggregates, with most in the invisible sub-micrometer range of 100 nanometers. Various technologies have been developed for identifying and filtering out exhaust PMs before the exhaust is released to the atmosphere.

As an example, PM sensors, also known as soot sensors, may be used in vehicles having internal combustion engines. A PM sensor may be located upstream and/or downstream of a diesel particulate filter (DPF), and may be used to sense PM loading on the filter and diagnose operation of the DPF. Typically, the PM sensor may sense a particulate matter or soot load based on a correlation between a measured change in electrical conductance (or current/resistance) between a pair of electrodes placed on a planar substrate surface of the sensor with the amount of PM deposited between the measuring electrodes. Specifically, the measured conductivity provides a measure of soot accumulation. As such, the PM sensor sensitivity may be affected by size of particulates accumulated on the measuring electrodes. For example, when a large particulate gets deposited between the measuring electrodes, a PM sensor current may quickly saturate, thereby reducing the sensitivity of the PM sensor to detect particulates depositing thereafter. In addition, large particulates deposited on the electrodes may lead to false indication of DPF degradation and unwarranted replacement of functioning filters. Furthermore, the distribution of the particulates on the PM sensor electrodes may also affect the current measured by the sensor, thus leading to errors in the output of the PM sensor. Herein, the PM sensor capturing the PMs exiting the DPF, may not truly reflect the DPF filtering capabilities.

One example PM sensor design is shown by Roth et al. in U.S. Pat. No. 8,823,401. Therein, a pair of planar adjacently placed interdigitated electrodes, connected to a common voltage source are used to independently detect PMs in the exhaust. As the PMs deposit on the interdigitated electrode pair due to electrostatic attraction between the charged PMs and the electrodes, the output of the two independent PM sensors are further analyzed and compared using extensive algorithms to derive meaningful information to distinguish larger particulates in the exhaust.

However, the inventors herein have recognized potential issues with such an approach. The PM sensors described by Roth et al. may continue to have issues with large particulates saturating the PM sensor current, and thereby affecting the PM sensor sensitivity. Additionally, the sensor output of Roth et al., requires analysis with extensive algorithms to derive meaningful information regarding PMs in the exhaust, leading to extended processing times and undesired delays in data output and diagnostics.

The inventors have identified an approach to partly address these issues while improving sensitivity of the PM sensors. In one example, the issues described above may be addressed by a method for adjusting engine operation responsive to a distribution of particulates on a plurality of electrode pairs positioned inside a common particulate matter (PM) sensor housing of a PM sensor. As such, each individual electrode pair of the plurality of electrode pairs may be connected to different voltage sources and current measured across each electrode pair may be summed to generate the total PM sensor current. As a result, PM accumulation across each individual electrode pair may be monitored independently, and particulate six distribution may be tabulated.

As one example, large particulates depositing on one of the electrode pairs may saturate the current measured across that particular electrode pair, while leaving the remaining electrode pairs unaffected. The technical effect of summing the current generated across the plurality of electrode pairs of the PM sensor to generate a total current of the PM sensor is that the total PM sensor current may not saturate and may continue to increase as PMs continue to get deposited on the remaining electrode pairs. In this way a more accurate measure of the exhaust PM load, and thereby the DPF PM load can be determined. As such, this improves the efficiency of filter regeneration operations, and reduces the need for extensive algorithms. In addition, by enabling more accurate diagnosis of an exhaust DPF, exhaust emissions compliance may be improved. As such, this reduces the high warranty costs of replacing functional particulate filters and exhaust emissions are improved and exhaust component life is extended.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

DETAILED DESCRIPTION

Figure 1:
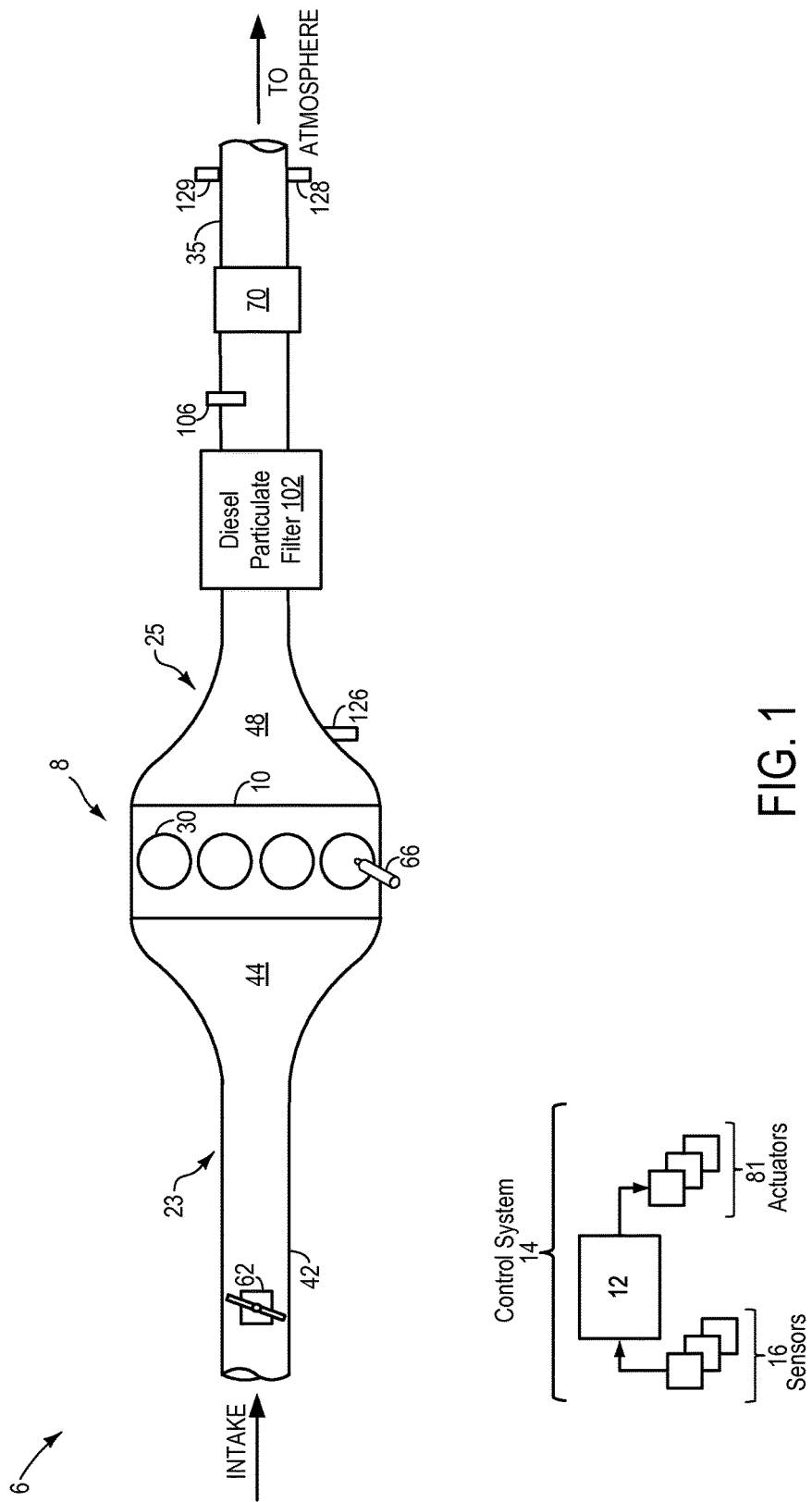
FIG. 1 shows a schematic diagram of an engine and an associated particulate matter (PM) sensor positioned in an exhaust flow.
Figure 2A:
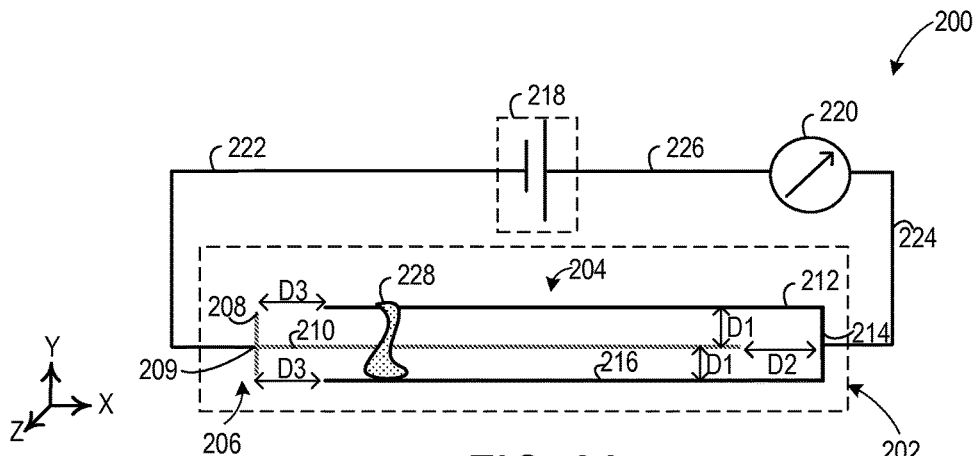
FIG. 2A shows a magnified view of an individual electrode pair of a plurality of electrode pairs of the PM sensor and an associated circuit for detecting PMs accumulated in the individual electrode pair.

The following description relates to sensing particulate matter (PM) in an exhaust flow of an engine system, such as the engine system shown in FIG. 1. An individual electrode pair of a PM sensor as shown in FIG. 2A may include a pair of interdigitated electrodes electrically coupled to a voltage source to generate a current based on particulates accumulated between the electrodes. A plurality of electrode pairs of the PM sensor (shown in FIG. 2B) may be connected to a plurality of voltage sources to independently measure the current across each of the electrodes and summed together to generate a total current of the PM sensor (FIG. 2C). A controller may be configured to perform a control routine, such as the routine of FIG. 3 to distinguish particulate size and regenerate the PM sensor based on the total current of the PM sensor. In addition, the controller may intermittently clean the PM sensor (as shown in the method presented at FIG. 4) to enable continued PM detection and perform diagnostics on a particulate filter positioned upstream of the PM sensor based on a duration between particulate filter regenerations (as shown in the method presented at FIG. 5). An example relation between the total current of the PM sensor and DPF soot load is depicted with reference to FIG. 6. In this way, by independently measuring the current across individual electrode pairs of the plurality of electrode pairs of the PM sensor and summing them to generate the total current of the PM sensor, any variations in measurement may be reduced. Overall, the functioning of the PM sensor to estimate the filtering capabilities of the DPF (and thereby to detect DPF leaks) may be increased and exhaust emissions compliance may be enhanced as PMs in the exhaust may be detected more reliably.

FIG. 1 shows a schematic depiction of a vehicle system 6. The vehicle system 6 includes an engine system 8. The engine system 8 may include an engine 10 having a plurality of cylinders 30. Engine 10 includes an engine intake 23 and an engine exhaust 25. Engine intake 23 includes a throttle 62 fluidly coupled to the engine intake manifold 44 via an intake passage 42. The engine exhaust 25 includes an exhaust manifold 48 eventually leading to an exhaust passage 35 that routes exhaust gas to the atmosphere. Throttle 62 may be located in intake passage 42 downstream of a boosting device, such as a turbocharger (not shown), and upstream of an after-cooler (not shown). When included, the after-cooler may be configured to reduce the temperature of intake air compressed by the boosting device.

Engine exhaust 25 may include one or more emission control devices 70, which may be mounted in a close-coupled position in the exhaust. One or more emission control devices may include a three-way catalyst, lean NOx filter, SCR catalyst, etc. Engine exhaust 25 may also include diesel particulate filter (DPF) 102, which temporarily filters PMs from entering gases, positioned upstream of emission control device 70. In one example, as depicted, DPF 102 is a diesel particulate matter retaining system. DPF 102 may have a monolith structure made of, for example, cordierite or silicon carbide, with a plurality of channels inside for filtering particulate matter from diesel exhaust gas. Tailpipe exhaust gas that has been filtered of PMs, following passage through DPF 102, may be measured in a PM sensor 106 and further processed in emission control device 70 and expelled to the atmosphere via exhaust passage 35. In the depicted example, PM sensor 106 is a resistive sensor that estimates the filtering efficiency of the DPF 102 based on a change in conductivity measured across the electrodes of the PM sensor. Herein, the PM sensor 106 is a resistive sensor that estimates a soot leakage of the DPF 102 based on a change in conductance measured across the electrodes of the soot sensor 106. If the soot emission from the DPF 102 as determined from the output of the PM sensor 106 is greater than the threshold soot emission, then the DPF 102 may be determined to be leaking and damaged, and in need of replacement. As such, when the conductance of the PM sensor reaches a threshold, the PM sensor may also be regenerated by heating the PM sensor until the soot particles are burned off. The response time for the accumulation of soot emission and thus the response time to achieve a threshold of conductance is a measure of DPF leakage. As such, the PM sensor may be regenerated by heating the sensor substrate via a heating element (not shown) to burn the accumulated soot particles from the surface of PM sensor 106. By intermittently regenerating the surface of soot sensor 106, it may be returned to a condition more suitable for collecting exhaust soot. In addition, accurate information pertaining to the exhaust soot level may be inferred from the sensor regeneration and relayed to the controller.

The vehicle system 6 may further include control system 14. Control system 14 is shown receiving information from a plurality of sensors 16 (various examples of which are described herein) and sending control signals to a plurality of actuators 81 (various examples of which are described herein). As one example, sensors 16 may include exhaust flow rate sensor 126 configured to measure a flow rate of exhaust gas through the exhaust passage 35, exhaust gas sensor (located in exhaust manifold 48), temperature sensor 128, pressure sensor 129 (located downstream of emission control device 70), and PM sensor 106. Other sensors such as additional pressure, temperature, air/fuel ratio, exhaust flow rate and composition sensors may be coupled to various locations in the vehicle system 6. As another example, the actuators may include fuel injectors 66, throttle 62, DPF valves that control filter regeneration (not shown), a motor actuator controlling PM sensor opening (e.g., controller opening of a valve or plate in an inlet of the PM sensor), etc. The control system 14 may include a controller 12. The controller 12 may be configured with computer readable instructions stored on non-transitory memory. The controller 12 receives signals from the various sensors of FIG. 1, processes the signals, and employs the various actuators of FIG. 1 to adjust engine operation based on the received signals and instructions stored on a memory of the controller. Example routines are described herein with reference to FIGS. 3-5.

Returning to FIG. 1, PM sensor 106 of FIG. 1 is disposed inside exhaust passage 35 with exhaust gases flowing from downstream of DPF 102 towards an exhaust tailpipe as indicated by the arrows. In some examples, the PM sensor 106 may be upstream to DPF to determine soot load on DPF. As such, the PM sensor 106 may include a protection tube that may serve to protect a PM sensor element housed within and may additionally serve to redirect exhaust gas flow over the PM sensor element. Typically, the PM sensor element includes a pair of planar interdigitated electrodes forming a "comb" structure that are connected to a single voltage source. By applying a voltage across the pair of planar interdigitated electrodes, an electric field may be generated within the gap between the electrodes, and any PM accumulated may alter the resistance between the electrodes, which can then be measured as a change in current across the electrodes. By monitoring the change in current, soot load on the PM sensor may be determined. Herein, PMs or soot is deposited onto interdigitated electrodes of the PM sensor element by way of electrostatic attraction of the charged soot particles to the sensor surface by the electric field generated by the planar interdigitated pair of electrodes. However, when larger particulates get deposited between the electrodes, thereby connecting multiple "combs" of the electrode, the PM sensor current may saturate. Thereafter, any PMs accumulating on the PM sensor electrode may not increase the current, thereby reducing the sensitivity of the PM sensor to detect PMs in the exhaust. In some examples, a leak in the DPF may be indicated, requiring unwarranted replacement of an otherwise functioning DPF.

The inventors have recognized that by independently connecting individual electrode pairs of the interdigitated comb structure to separate voltage sources and separate measurement devices, and thereby monitoring current across each of the individual electrode pairs, it may be possible to reduce PM sensor current saturation due to large particulate impingement, for example.

An individual electrode pair is shown in schematic view 200 of FIG. 2A. Turning now to FIG. 2A, view 200 shows an individual electrode pair 202 coupled to a measurement circuit comprising of a voltage source 218 and a measurement device 220. Herein the individual electrode pair 202 may further include a positive electrode 204 and a negative electrode 206.

The positive and negative electrodes 204 and 206 may be typically manufactured from metals such as platinum, gold, osmium, rhodium, iridium, ruthenium, aluminum, titanium, zirconium, and the like, as well as, oxides, cements, alloys and combination comprising at least one of the foregoing metals. The electrodes 204 and 206 are formed on a substrate (not shown) of the PM sensor that is typically manufactured from highly electrically insulating materials. Possible electrically insulating materials may include oxides such as alumina, zirconia, yttria, lanthanum oxide, silica, and combinations comprising at least one of the foregoing, or any like material capable of inhibiting electrical communication and providing physical protection for the individual pair of interdigitated electrodes 202.

The negative electrode 206 may include a first electrode wire or pad or "tine" 208 and a second electrode wire or pad or "tine" 210 which are connected at a junction 209. Herein, the first electrode wire 208 extends along a first direction (along Y-axis, for example) to a first distance given by the length of the first electrode wire 208. The second electrode wire may extend along a second direction (along X-axis, for example) orthogonal to the first direction, and further may extend to a second distance, wherein the second distance is greater than the first distance, for example. Herein, the second distance may include the length of the second electrode wire 210. As seen in schematic view 200, the first electrode wire 208 and the second electrode wire 210 of the negative electrode 206 forms a "T-shaped" junction 209. In one example, the junction 209 may be formed midway along the length of the first electrode wire 208. As such, at the junction 209, the first electrical wire 208 may be electrically coupled to the second electrode wire 210 of the negative electrode 206. Together, the first electrode wire 208 and the second electrode wire 210 make up the negative electrode 206, for example.

The positive electrode 204 of the individual electrode pair 202 may include a single electrode wire or pad or "tine" made up of multiple segments 212, 214, and 216 separated from each of the first electrode wire 208 and the second electrode wire 210, thereby generating a gap in which the charged PMs may get trapped. Herein, segments 212 and 216 may be positioned on either side of the second electrode wire 210 of the negative electrode, further equidistant (at distance D1, for example) from the second electrode wire 210. For example, the distance may include a space with no components there-between.

The first segment 212 of the positive electrode 204 may extend along the second direction (along X-axis, for example), to a third distance, the third distance being longer than each of the first distance and the second distance. In addition, the first segment 212 of the positive electrode 204 may be connected to a second, orthogonal segment 214 and further connected to a third segment 216. Together, the three segments of the positive electrode 204 surround or encompass the second electrode wire 210, and are further separated and electrically isolated (or decoupled) from each of the first electrode wire 208, and the second electrode wire 210. The first segment 212 is separated from the third segment 216 by a distance which equals the length of the second segment 214 (or 2D1), for example. In some examples, the segments 212, 214, and 216 may be a single continuous electrically coupled electrode wire, together forming the positive electrode 204. However, the positive electrode 204 and the negative electrode 206 may be decoupled from each other.

As described earlier, the second electrode wire 210 of the negative electrode is coupled to first electrode wire 208 at junction 209. However, the second electrode wire 210 includes an unattached end which is separated by a distance from each of the first segment 212, second segment 214 and third segment 2116 of the positive electrode. The distance between the unattached end of the second electrode wire 210 and the second segment 214 of the positive electrode is D2, while the distance between the unattached end of the second electrode wire 210 and each of the first segment 212 and the third segment 216 of the positive electrode is D1.

The negative electrode 206 is electrically coupled to a negative terminal of the voltage source 218 via an electrical connection 222. Furthermore, the positive electrode 204 is electrically coupled to a measurement device 220 via electrical connection 224, and further connected to a positive terminal of the voltage source 218 via electrical connection 226. Herein the measurement device 220 is connected between the positive electrode and the positive terminal of the voltage source 218. In some examples, the measurement device may be between the negative electrode and the negative terminal of the voltage source 218. As such, the electric field generated between the positive and the negative electrode may aid in trapping electrically charged soot particles between them, thereby forming soot bridges.

The electrical connections 222, 224 and 226, the voltage source 218 and the measurement device 220 may be part of an electric circuit that may be housed outside the exhaust passage 35 (as one example, <1 meter away). Further, the voltage source 218 and the measurement device of the electrical circuit may be controlled by a controller, such as controller 12 of FIG. 1, so that particulate matter collected at the PM sensor may be used for diagnosing leaks in the DPF, for example. As such, the measurement device 220 may be any device capable of reading a resistance change across the electrodes, such as a voltmeter. In some examples, the measurement device 220 may be a current measuring device such as an ammeter. As PM or soot particles 228 get deposited between the positive electrode 204 and the negative electrode 206, the resistance between the electrode pair may start to decrease, which is indicated by an increase in the current measured by the measurement device 220. The controller 12 may be able to determine the resistance between the individual electrode pair 202 as a function of current measured by the measurement device 220 and infer a corresponding PM or soot load on the individual electrode pair 202 of the PM sensor. In this way, by connecting the individual electrode pair to a voltage source, it may be possible to determine the current across the individual electrode pair based on PMs accumulated between the electrodes of the individual electrode pair 202. Herein, a length of the PM deposited between the individual electrode pair 202 may be determined based on the resistance (and further based on current) measured by the measurement device 220. When the accumulated PMs get long enough thereby extending along the gap between the positive electrode and the negative electrode, and touching the positive electrode and the negative electrode, a soot bridge may be formed. When the soot bridge is formed, the current measured across the positive and the negative electrode may saturate, for example. Thus, a large particulate 228 extending across the positive electrode 204 and the negative electrode 206 may saturate the current measured by the measurement device 220, for example.

In PM sensors including interdigitated electrodes that are connected to a single voltage supply, the soot bridge formed across one or more pairs of positive and negative "tines" of the PM sensor electrodes may saturate the current measured across the PM sensor. Thereafter, the current measured across the PM sensor electrodes may not sense any of the particulates further depositing between the electrodes of the PM sensors. The inventors have recognized that by using plurality of interdigitated electrodes and by independently connecting each of them to separate voltage sources as shown in FIG. 2B, the PM sensor may not be affected by large particulates depositing between the electrodes of the PM sensor, thereby continuing to detect PMs in the exhaust.

Figure 2B:
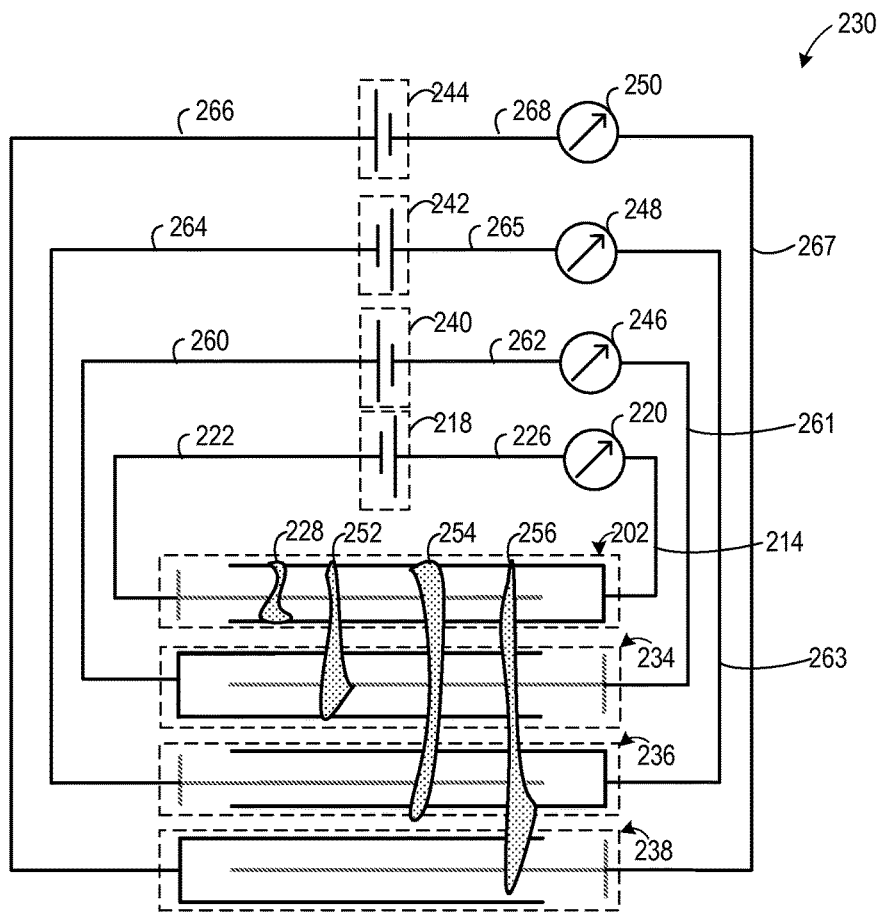
FIG. 2B shows the plurality of electrode pairs of the PM sensor with plurality of voltage sources for detecting PMs in the exhaust flow.
Figure 2C:
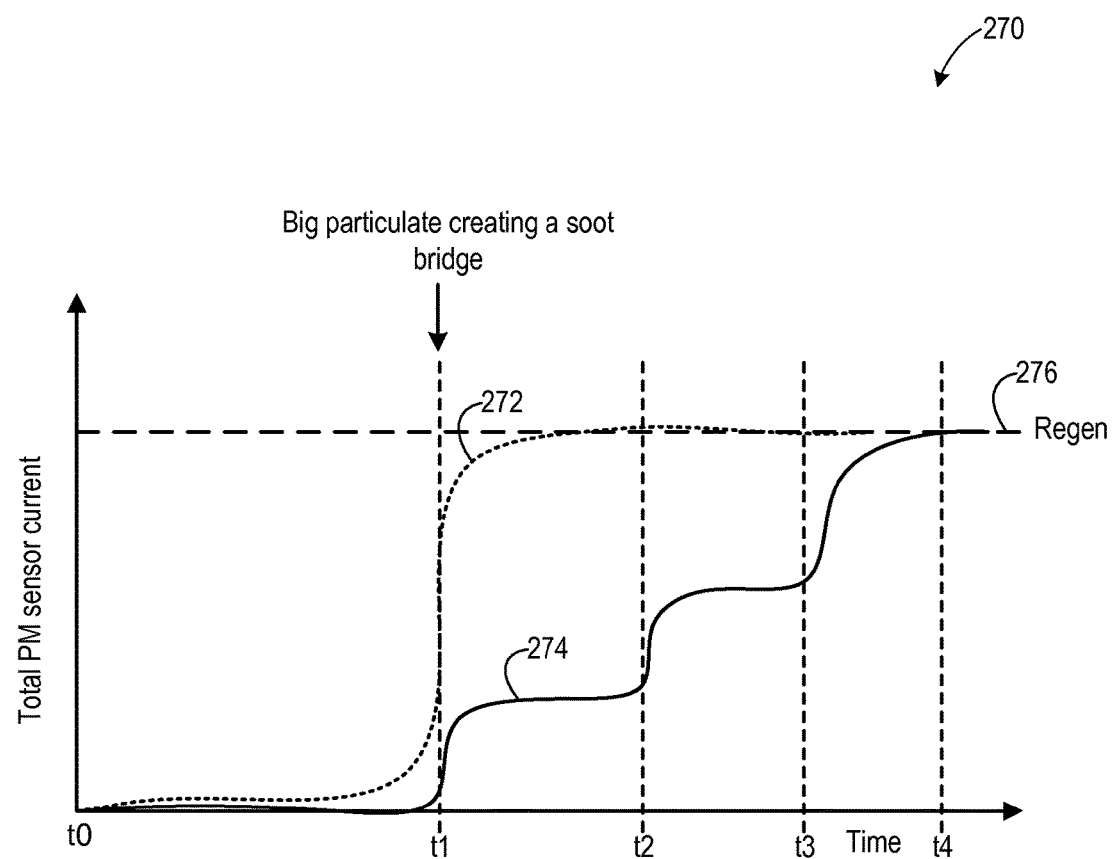
FIG. 2C shows an example current generated across the plurality of electrode pairs of the PM sensor.

Turning now to FIG. 2B, a schematic view 230 of an example embodiment of interdigitated electrodes of a particulate matter (PM) sensor (such as PM sensor 106 of FIG. 1) and a PM detection circuit is shown. Herein, the PM sensor may include plurality (herein four) of interdigitated electrode pairs 202, 234, 236, and 238 electrically coupled to plurality (herein four) of voltage sources 218, 240, 242, and 244 as shown in FIG. 2B.

As such, the details of each interdigitated electrode pairs 202, 234, 236, and 238 and their corresponding positive and negative electrodes of the plurality of electrode pairs of view 230 may be similar to the individual electrode pair 202 and its positive and negative electrodes 204 and 206 of schematic view 200 described above.

In one example the individual electrode pair 202 of FIG. 2B may be a first individual electrode pair and may further be similar to individual electrode pair 202 explained in detail with reference to FIG. 2A. In addition to the individual electrode pair 202, the PM sensor shown in view 230 may include a second individual electrode pair 234, further separated from the first individual electrode pair 202 by a gap. Furthermore, the second individual electrode pair 234 may include a positive electrode surrounding a negative electrode further isolated and separated by a distance (wherein the positive electrode and the negative electrode of electrode pair 234 are similar to the positive and negative electrode 204 and 206 explained with reference to FIG. 2A, for example). Further more, the positive electrode may be connected to a positive terminal of the second voltage source 240 via connecting wire 260. Similarly, the negative electrode of the second individual electrode pair 234 may be connected to a measurement device 246 via connecting wire 261, and further to a negative terminal of the voltage source 240 by connecting wire 262. Herein, the voltage source 240 may be different from voltage source 218, and further measurement device 246 may be different from the measurement device 220. In addition, the second individual electrode pair 234 may be separated from individual electrode pair 202 by a distance. In some examples, the measurement device 246 may be connected between the positive electrode of the individual electrode pair 234 and the positive terminal of the voltage source 240. In some more examples, the negative electrodes of successive individual electrode pairs 202 and 234 may be diagonally opposite to one another.

The PM sensor of view 230 may further include a third individual electrode pair 236 and a fourth individual electrode pair 238. As such the details of the third and fourth individual electrode pairs may be similar to the first and second individual electrode pairs discussed earlier. Briefly, the third individual electrode pair 236 may include a positive electrode surrounding a negative electrode further isolated and separated by a distance (wherein the positive electrode and the negative electrode of electrode pair 234 are similar to the positive and negative electrode 204 and 206 explained with reference to FIG. 2A, for example). Further more, the positive electrode may be connected to a third measurement device 248 via connecting wire 263 and further connected to a positive terminal of a third voltage source 242 via connecting wire 265. Similarly, the negative electrode of the third individual electrode pair 236 may be connected to a negative terminal of the third voltage source 242 by connecting wire 264. Herein, the third voltage source 242 may be different from each of the first voltage source 218 and the second voltage source 240, and further the third measurement device 248 may be different from each of the first measurement device 220 and the second measurement device 246. In addition, the third individual electrode pair 236 may be closer to the second individual electrode pair 234 than the first individual electrode pair 202, further separated from the second individual electrode pair 234 by a distance. In some examples, the separation between the third individual electrode pair 236 and the second individual electrode pair 234 may be similar to the separation between the first individual electrode pair 202 and the second individual electrode pair 234. In other examples, the separation between successive individual electrode pairs may be different. In some examples, the measurement device 248 may be connected between the negative electrode of the individual electrode pair 236 and the negative terminal of the third voltage source 248. In some more examples, the negative electrodes of successive individual electrode pairs may be diagonally opposite to one another.

In addition, the fourth individual electrode pair 238 may include a positive electrode surrounding a negative electrode further isolated and separated by a distance (wherein the positive electrode and the negative electrode of electrode pair 234 are similar to the positive and negative electrode 204 and 206 explained with reference to FIG. 2A, for example). Furthermore, the negative electrode of the fourth individual electrode pair 238 may be connected to a fourth measurement device 250 via connecting wire 267 and further connected to a negative terminal of a fourth voltage source 244 via connecting wire 268. Similarly, the positive electrode of the fourth individual electrode pair 238 may be connected to a positive terminal of the fourth voltage source 244 by connecting wire 266. Herein, the fourth voltage source 244 may be different from each of the first voltage source 218, the second voltage source 240 and the third voltage source 242, and further the fourth measurement device 250 may be different from each of the first measurement device 220, the second measurement device 246 and the third measurement device 248. In addition, the fourth individual electrode pair 238 may be closer to the third individual electrode pair 236 than the first individual electrode pair 202 and the second individual electrode pair 234, further separated from the third individual electrode pair 236 by a distance. In some examples, the separation between the fourth individual electrode pair 238 and the third individual electrode pair 236 may be similar to the separation between the first individual electrode pair 202 and the second individual electrode pair 234, and further similar to the separation between the second individual electrode pair 234 and the third individual electrode pair 236. In other examples, the separation between successive individual electrode pairs may be different. In some examples, the measurement device 250 may be connected between the positive electrode of the individual electrode pair 238 and the positive terminal of the fourth voltage source 250. In some more examples, the negative electrodes of successive individual electrode pairs may be diagonally opposite to one another.

Herein, the PM sensor consists of four individual electrode pairs, however, the PM sensor may include more individual electrode pairs without deviating from the scope of the disclosure. As such, the electrical connections or connecting wires connecting the plurality of individual electrode pairs to the corresponding plurality of voltage sources and plurality of measurement devices may be part of an electric circuit that may be housed outside the exhaust passage 35 (as one example, <1 meter away). As such, the plurality of measurement devices may be devices capable of reading resistance change across the electrodes, such as voltmeter. In some examples, the measurement devices may be current measuring devices such as ammeter. Further, the plurality of voltage sources (such as voltage sources 218, 240, 242, 244 of view 230 of FIG. 2B) and the plurality of measurement devices (such as measurement devices 220, 246, 248, and 250 of view 230 of FIG. 2B) of the electrical circuit may be controlled by a controller, such as controller 12 of FIG. 1, so that particulate matter collected at the PM sensor may be used for diagnosing leaks in the DPF, as explained below with reference to FIG. 2C.

Thus, an example particular matter (PM) sensor system may include a PM sensor including a plurality of planar interdigitated electrode pairs and plurality of voltage sources wherein each individual planar interdigitated electrode pair of the plurality of interdigitated electrode pairs includes a positive electrode and a negative electrode, the positive electrode electrically coupled to a positive terminal of a voltage source via a measurement device, the negative electrode electrically coupled to a negative terminal of the voltage source, and wherein the individual electrode pairs are isolated from one another by an insulating gap. Herein, the negative electrode of each of the planar interdigitated electrode pair may include a first electrode wire extending a first distance along a first direction and a second electrode wire extending a second distance along a second direction, the first direction is orthogonal to the second direction, and the second distance is greater than the first distance. Further, first electrode wire of the negative electrode may be electrically coupled to the second electrical wire forming a junction between the first electrode wire and the second electrode wire, and further electrically coupled to the negative terminal of the voltage source. Furthermore, the positive electrode of each of the planar interdigitated electrode pair comprises a positive electrode wire adjacent to each of the first electrode wire and the second electrode wire enveloping the second electrode wire of the negative electrode and further isolated from each of the first electrode wire and second electrode wire of the first negative electrode and further connected to the positive terminal of the voltage source.

Figure 4:
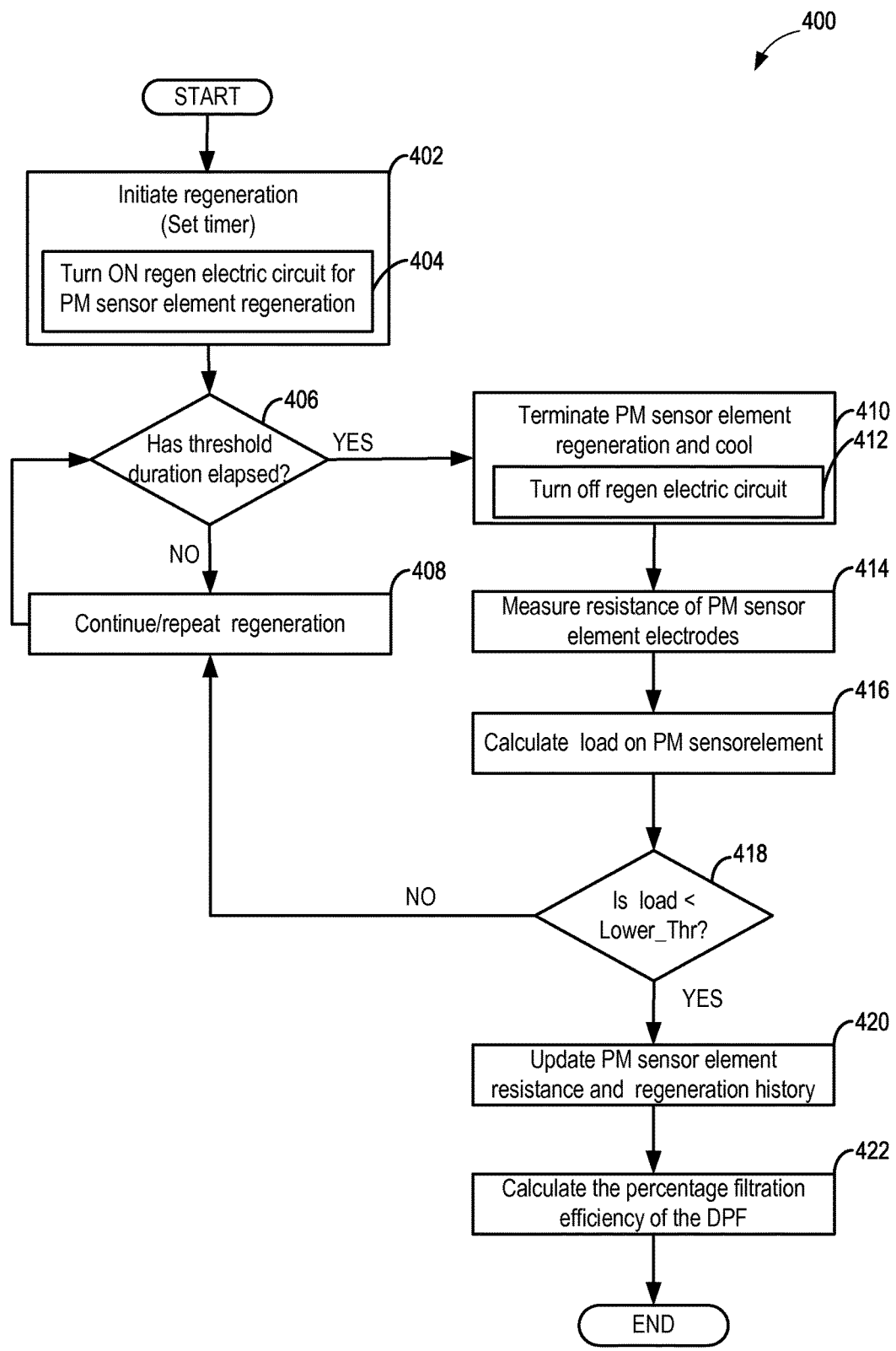
FIG. 4 shows a chart depicting a method for performing regeneration of the PM sensor.
Figure 5:
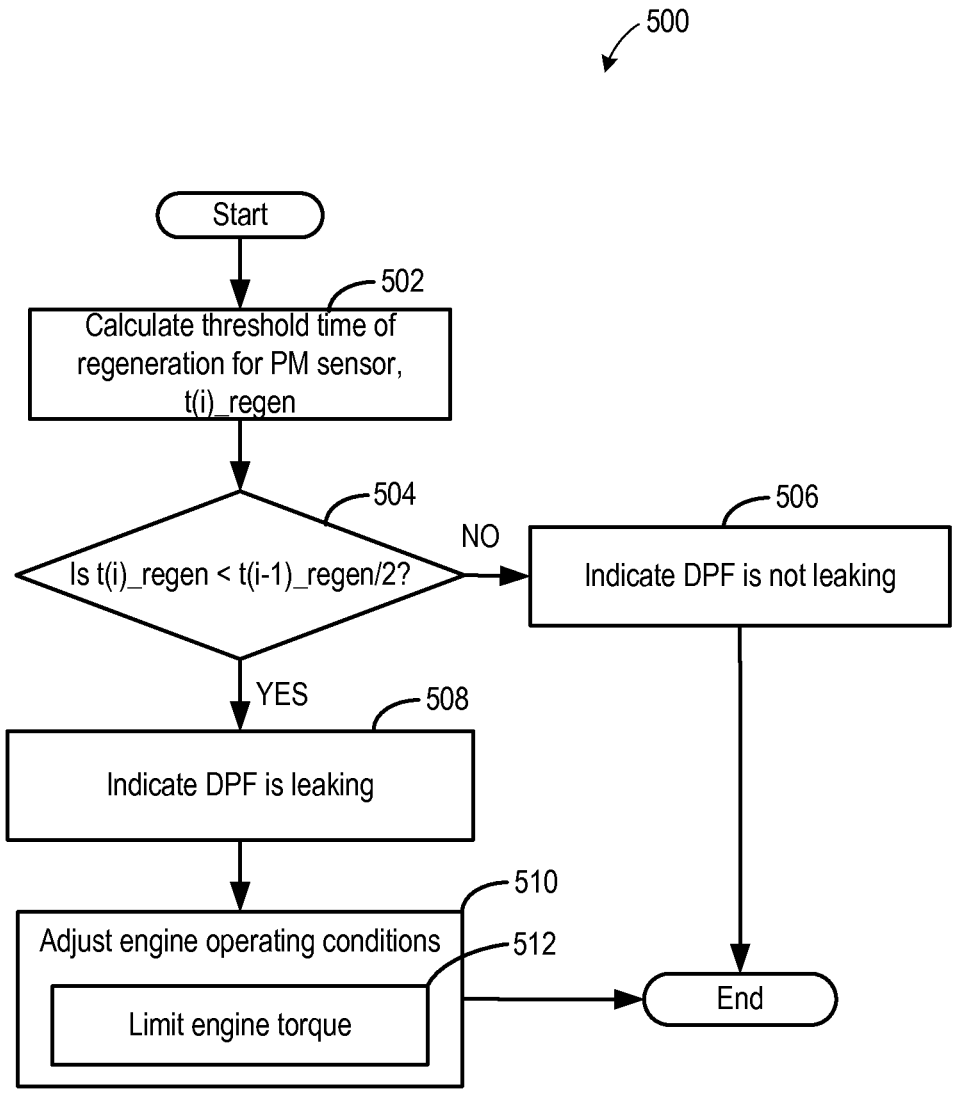
FIG. 5 shows a flow chart depicting a method for diagnosing leaks in a particulate filter positioned upstream of the PM sensor.

The PM sensor system may further include a controller with computer readable instructions stored on non-transitory memory for accumulating PMs across each of the positive electrode and the negative electrode of the planar interdigitated electrode pair by accumulating the PMs between one or more of first electrode wire, the second electrode wire, and the positive electrode wire as discussed below with reference to FIG. 2C. Herein, the PM sensor may be positioned downstream of a particulate filter in an engine exhaust passage, and the controller may include further instructions for generating a current across each of the planar interdigitated electrode pair, summing the current generated across each of the planar interdigitated electrode pair and generating a total current of the PM sensor (FIG. 3), and regenerating the PM sensor when the total current is higher than a threshold (FIG. 4). In addition, the controller may further include instructions for indicating leak in the particulate filter based on a duration between regenerations of the PM sensor (FIG. 5).

FIGS. 2A-2B show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example.

Turning now to FIG. 2C, plot 270 shows current generated across the plurality of electrode pairs described with reference to FIG. 2B. Specifically, plot 270 compares the total current generated in the PM sensor embodiment including a plurality of planar interdigitated electrode pairs connected to plurality of voltage sources with an example PM sensor including an interdigitated "comb" electrode structure with a single voltage source. The total PM sensor current is shown along the vertical axis, and time is shown along the horizontal axis. Line 276 may indicate a threshold current corresponding to PM sensor regeneration.

In FIG. 2C, curve 272 represents the total PM sensor current generated in an example PM sensor including continuous interdigitated electrodes coupled to a single voltage source. Herein, the PM sensor may include a positive electrode comprising of continuous "tines" wherein all the "tines" are coupled to a positive terminal of the single voltage source. Similarly, the PM sensor may also include a negative electrode, again comprising of continuous "tines" wherein all the "tines" are coupled to a negative terminal of the single voltage source. In addition, the PM sensor may include a single measurement device coupled between the positive electrode and the voltage source or the negative electrode and the voltage source. As PMs accumulate between the positive electrode and the negative electrode of the PM sensor, the change in resistance may be detected by the measurement device, and a current may be generated corresponding to the change in resistance. Between t0 and t1, the PM sensor may accumulate PMs and generate total PM sensor current as indicated by curve 272.

At t1, a large particulate may get deposited between one or more of electrode pairs of the PM sensor forming a soot bridge across the electrodes of the PM sensor, causing the total PM sensor current to saturate (curve 272). Herein, the total PM sensor current as measured by the single measurement device coupled across the electrodes may reach the threshold for regeneration (line 276) quickly. Thereafter, PMs accumulating between the electrodes may not cause an increase in the total PM sensor current (curve 272). As such, with a single voltage source and a single measurement device coupled across the interdigitated electrodes of the PM sensor, the total PM sensor current measured by the measurement device may have weak dependence to the size and/or length of the bridge, and may also not depend on the number of bridges. Herein, the DPF located upstream of the PM sensor may be wrongly determined to be leaking leading to unwanted replacements of the otherwise functioning DPF.

The inventors have recognized that by including plurality of voltage sources and plurality of measurement devices coupled across individual electrode pairs as explained with reference to FIG. 2B, the total PM sensor current may be generated by summing current across individual electrode pairs. Herein, curve 274 represents the total PM sensor current generated by summing current across individual electrode pairs shown in FIG. 2B.

Returning to FIG. 2C, the first current ($I_1$) may be the current generated across the first individual electrode pair 202 may be measured by the first measurement device 220. As such, when PMs accumulate between the positive electrode and the negative electrode of the individual electrode pair, current I may be generated. Similarly, the current generated across the second individual electrode pair 234 as measured by the second measurement device 246 may be $I_2$. Likewise, the current generated across the third individual electrode pair 236 as measured by the third measurement device 248 may be $I_3$, and the current generated across the fourth individual electrode pair 238 as measured by the fourth measurement device 250 may be $I_4$. Herein the PM sensor shown in FIG. 2B includes four individual electrode pairs. However, the PM sensor may include more than four individual electrode pairs, for example. Thus, the total PM sensor current may be generated by summing the current generated across the individual electrode pairs and may be mathematically written as $I_{total} = \Sigma_{i=1}^{n} I_i$ where i may indicate the number of individual electrode pairs included the PM sensor design. In the example embodiment shown in FIG. 2B, i equals four. Thus, in such an example, the total PM sensor current $I_{total} = I_1 + I_2 + I_3 + I_4$.

Returning to FIG. 2C, curve 274 represents $I_{total}$ of the PM sensor as explained above. Between t0 and t1, the total PM sensor current may be represented by curve 274. At t1, a large particulate may accumulate between the electrodes of the first individual electrode pair, for example (such as PM 228 across electrode of individual electrode pair 202 of FIG. 2B, for example). In some example, PM 228 may be formed by PMs accumulating over time thereby forming a large soot bridge across the electrodes of the first individual electrode pair. The large particulate (or the soot bridge) accumulating across the electrodes of the first individual electrode pair, may cause an increase in the total PM sensor current at time t1 (curve 274). In some examples, the current across the first individual electrode $I_1$ as measured by the first measurement device 220 may saturate, however, the current across the other individual electrode pairs may not saturate, and hence the total PM sensor current may remain below the threshold current for PM sensor regeneration (line 276) for example. As such, when PM 228 gets accumulated and grows along the Y-axis thereby forming a soot bridge connecting both the positive and the negative electrode of the first electrode pair 202, the current $I_1$ measured across the first measurement device may reach a first threshold, the first threshold may be a saturation current for the first individual electrode pair, for example. Herein, the current $I_1$ may be used to determined PM (228) size, and may further used to determine PM (228) length, for example. In some examples, the threshold may be based on the PM size and/or PM length and further based on resistance measured across the electrodes. As such, the total PM sensor current that may be given by $I_{total} \sim I_1$ where the currents measured by the remaining individual electrode pairs may be small.

Between, t2 and t3, the PMs may continue to get accumulated across the PM sensor, and the plurality of electrodes may continue to detect the PMs as indicated by a steady increase in the total PM sensor current (curve 274). However, at t2, large particulate (such as PM 252 across individual electrode pairs 202 and 234 of FIG. 2B, for example) may get deposited across plurality of electrode pairs leading to an increase in the total PM sensor current (curve 274). For example, PM 252 may be a large particulate extending along the Y-axis covering multiple electrode pairs. In some examples, the PM 252 may correspond to soot bridge forming across multiple electrode of successive individual electrode pairs 202 and 234 as PMs in the exhaust accumulate over time. Herein, the total PM sensor current $I_{total}$ may experience an increase as shown by curve 274, and the total PM sensor current $I_{total} \sim I_1 + I_2$ ($I_3$ and $I_4$ may be small, for example), however still remaining below the threshold current for PM sensor regeneration (line 276). Herein, the total PM sensor current may represent current summed across multiple individual electrode pairs. Said another way, the current as measured by the first and the second measurement devices 220 and 246 may be summed by the controller to determine the total PM sensor current. The currents measured by the third and the fourth measurement devices 248 and 250 may continue to remain small. The large particulate extending across multiple electrode pairs may cause the currents as measured by the corresponding measurement devices to reach a second threshold, the second threshold may be a saturation current for the first and the second individual electrode pairs, for example. In some examples, the second threshold may be larger than the first threshold.

Similarly, between time t2 and t3, the multiple individual electrode pairs may continue to capture PMs in the exhaust. However, at time t3, large particulate (such as PM 254 across individual electrode pairs 202, 234 and 236 of FIG. 2B, for example) may get deposited across plurality of electrode pairs leading to an increase in the total PM sensor current (curve 274). For example, PM 254 may be a large particulate extending along the Y-axis covering multiple electrode pairs. As explained earlier, the PM 254 may correspond to a soot bridge forming across multiple electrodes of successive individual electrode pairs 202, 234 and 236 as PMs in the exhaust accumulate over time. Herein, the total PM sensor current $I_{total}$ may experience an increase as shown by curve 274, and the total PM sensor current $I_{total} \sim I_1 + I_2 + I_3$ ($I_4$ may be small, for example), however still remaining below the threshold current for PM sensor regeneration (line 276). Herein, the total PM sensor current may represent the current as measured by the first, the second and the third measurement devices 220, 246 and 248 that may be summed by the controller to determine the total PM sensor current, for example. The currents measured by the fourth measurement devices 250 may continue to remain small ($I_4$~0). The large particulate extending across multiple electrode pairs may cause the currents as measured by the corresponding measurement devices to reach a third threshold, the third threshold may be a summation of saturation currents for the first, the second and the third individual electrode pairs, for example. In some examples, the third threshold may be larger than each of the second threshold and the first threshold.

Between time t3 and t4, the multiple individual electrode pairs may continue to capture PMs in the exhaust. However, at time t4, large particulate (such as PM 256 across all four individual electrode pairs of FIG. 2B, for example) may get deposited across plurality of electrode pairs leading to an increase in the total PM sensor current (curve 274). For example, PM 256 may be a large particulate extending along the Y-axis covering multiple electrode pairs. Herein, the total PM sensor current $I_{total}$ may experience an increase as shown by curve 274, and the total PM sensor current $I_{total}$~$I_{1+}+I_2+I_3+I_4$ and the total PM sensor current may reach the threshold for PM sensor regeneration (line 276). Herein, the total PM sensor current may represent the current as measured by the first, the second, the third and the fourth measurement devices 220, 246, 248 and 250 that may be summed by the controller to determine the total PM sensor current, for example. The large particulate extending across multiple electrode pairs may cause the currents as measured by the corresponding measurement devices to reach a fourth threshold, the fourth threshold may be a summation of saturation currents for the first, the second, the third and the fourth individual electrode pairs, for example. In some examples, the fourth threshold may correspond to the regeneration threshold for the PM sensor. Once the total PM sensor current reaches the regeneration threshold, indicating that the exhaust PM load has reached the threshold load, the PM sensor may need to be regenerated as described in FIG. 4. Briefly, during conditions when the exhaust PM load of the PM sensor is higher than the threshold load, the PM sensor may be regenerated by heating the sensor substrate via a heating element to burn the accumulated soot particles from the surface of PM sensor. By intermittently regenerating the surface of PM sensor, it may be returned to a condition more suitable for collecting exhaust PMs. In addition, accurate information pertaining to the exhaust PM level may be inferred from the sensor regeneration and relayed to the controller.

In this way, by summing the current across multiple individual electrode pairs, PM sensor may detect PMs in the exhaust more accurately, and not be affected by large particulates depositing on the electrodes, for example. The technical effect of summing the currents generated across multiple individual electrode pairs is that the PM sensor may detect PMs exiting the DPF more accurately, and hence diagnose the DPF for leaks in a more reliable fashion.

Thus, an example method may be performed by the controller as described with reference to FIG. 3 to determine exhaust PM levels more accurately and reliably. As such, the method may include accumulating particulate matter (PM) in an engine exhaust across each individual electrode pair of a plurality of electrode pairs located inside a PM sensor, independently generating a current across the each individual electrode pair responsive to accumulated particulate matter, distinguishing particulate matter size based on the current, and summing the current across a plurality of electrode pairs to generate a total current of the PM sensor. Herein, the total current may increase proportion to the particulate matter size. The method may further include regenerating the PM sensor when the total current of the PM sensor is greater than a threshold current. The method may further include indicating a leak in a particulate filter positioned upstream of the PM sensor when a duration between regenerations of the PM sensor is lower than a threshold and not indicating the leak in the particulate filter when the duration between regenerations of the PM sensor is greater than the threshold. Herein, each individual electrode pair of the plurality of electrode pairs includes a positive pad connected to a positive terminal of a voltage source and a negative pad connected to a negative terminal of the voltage source, the positive pad surrounding the negative pad and further separated by a distance.

Figure 3:
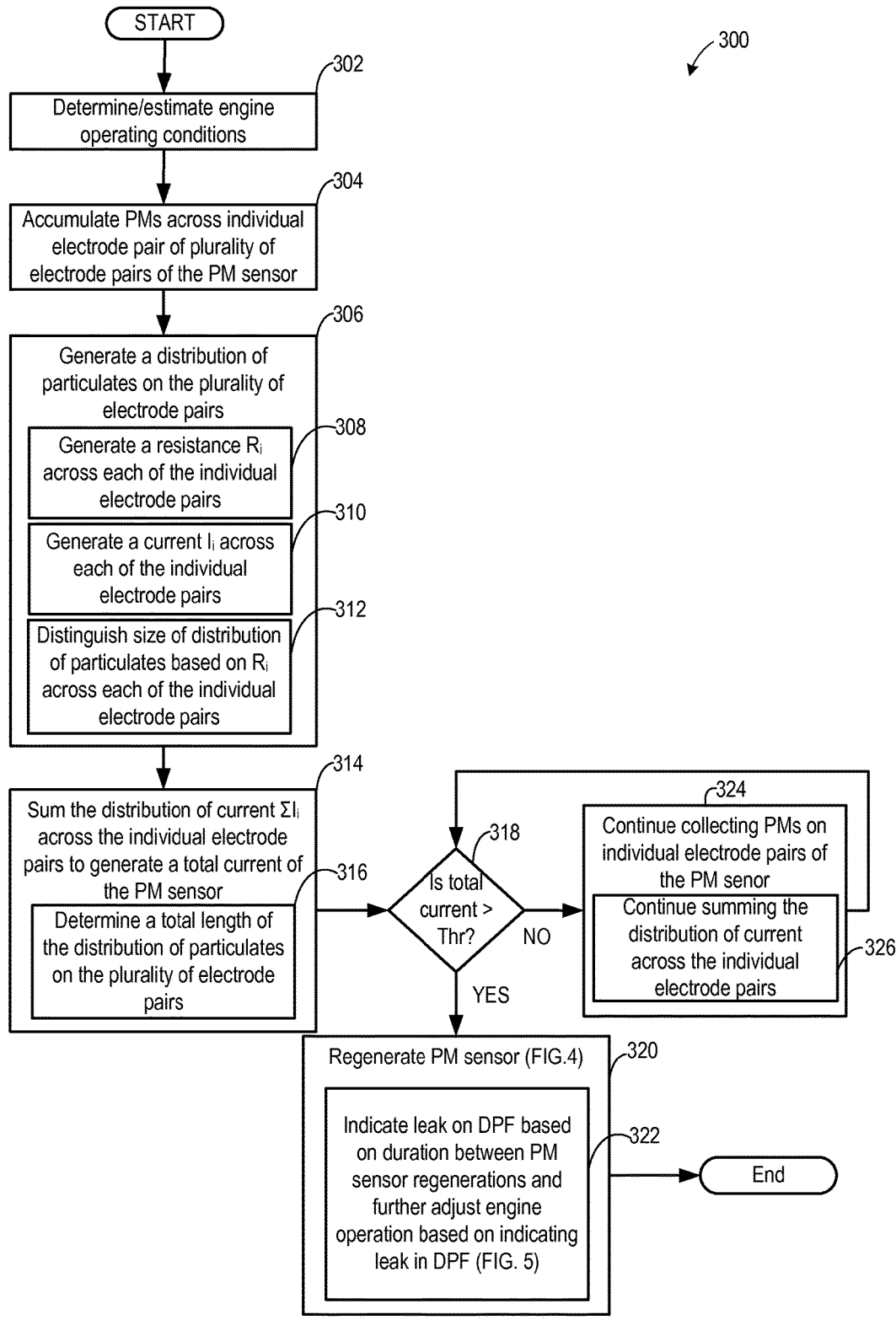
FIG. 3 shows a high level flow chart for operating the PM sensor to distinguish particulate size and regenerate the PM sensor based on a sum total of current generated across the individual electrode pairs of the plurality of electrode pairs of the PM sensor.

Turning now to FIG. 3, a method for operating the PM sensor to distinguish particulate size and regenerate the PM sensor based on a sum total of current generated across the individual electrode pairs of the plurality of electrode pairs of the PM sensor in shown. Instructions for carrying out method 300 and the rest of the methods included herein may be executed by a controller based on instructions stored on a memory of the controller and in conjunction with signals received from sensors of the engine system, such as the sensors described above with reference to FIGS. 1, 2A and 2B. The controller may employ engine actuators of the engine system to adjust engine operation, according to the methods described below.

At 302, method 300 includes determining engine operating conditions. Engine operating conditions determined may include, for example, engine speed, engine temperature, various exhaust air-fuel ratios, various exhaust temperatures, PM load on PM sensor, PM load on DPF, load on an exhaust LNT, ambient temperature, duration (or distance) elapsed since a last regeneration of PM sensor and DPF, etc. At 304, method 300 includes accumulating soot or PMs across individual electrode pairs of plurality of electrode pairs of the PM sensor. Herein, the PMs exiting the DPF may be collected across the electrodes of the PM sensor. The PM sensor may include multiple individual electrode pairs (as shown in FIG. 2B, for example). As PMs get accumulated across individual electrode pairs, current may be measured across the plurality of measurement devices. As such, the current measured by the measurement device may be used to generate the size of the PM deposited on the electrodes, for example. Larger particulates may overlap over plurality of electrodes thereby generating larger PM sensor current summed across plurality of measurement devices, for example. Likewise, smaller particulates may span over fewer electrode pairs, thereby generating a smaller PM sensor current.

Next at 306, method 300 includes generating a distribution of particulates on the plurality of electrode pairs. Generating a distribution of particulates may additionally and/or optionally include generating resistance $R_i$ across each of the individual electrode pairs of the plurality of electrode pairs of the PM sensor at 308 and further include generating a current $I_i$ across the individual electrode pair of the plurality of electrode pairs of the PM sensor. As explained earlier, when a particulate is deposited across an electrode pair, a current is measured across the measurement device coupled across the electrode pair, for example. The particulate deposited across the electrode pair may further cause a decrease in resistance $R_i$ and as such, the size of the particulate may be determined based on the resistance $R_i$ at 312, for example.

The method then proceeds to 314, where the distribution of current $I_i$ across the individual electrode pairs of the plurality of electrode pairs of the PM sensors may be summed to generate a total current $I_{total}$ of the PM sensor. Mathematically, the summation of the current across individual electrode pairs may be written as $I_{total}=\Sigma_{i=1}^{n}I_i$ where i may indicate the number of individual electrode pairs included the PM sensor design. In the example embodiment shown in FIG. 2B, i equals four. Thus, in such an example, the total PM sensor current $I_{total}=I_1+I_2+I_3+I_4$. Furthermore, method 300 includes determining a total length of the distribution of particulates on the plurality of electrode pairs of the PM sensor at 316.

Method 300 then proceeds to 318 where it may be determined if the total current $I_{total}$ is lower than a threshold, Thr. The threshold Thr, may be the threshold current that corresponds to PM sensor regeneration threshold. In some examples, the threshold Thr may be based on the PM load of the PM sensor above which the PM sensor may need to be regenerated. If the total current is lower than the threshold Thr, indicating that the PM sensor has not yet reached the threshold for regeneration, method 300 proceeds to 324, where the PMs may be continued to be collected across individual electrode pairs of the plurality of electrode pairs and then at 328, the currents generated across the plurality of individual electrode pairs of the PM sensor may be continued to be summed as explained earlier. The method then returns to 318, where the total current may be intermittently checked to determine if the PM sensor has reached regeneration threshold, for example.

If the total current is greater than the threshold Thr, then method proceeds to 320 where the PM sensor may be regenerated as described with reference to FIG. 4 and further at 322 method 300 includes indicating leak in DPF positioned upstream of the PM sensor based on a duration between PM sensor regenerations and further adjusting engine operation based on indicating leak in the DPF as explained with reference to FIG. 5. In this way, diagnostics on the DPF may be performed reliably and accurately by measuring and summing the current generated across plurality of individual electrode pairs that are connected to plurality of voltage sources and further connected to plurality of measurement devices.

Thus, an example method may include adjusting engine operation responsive to a distribution of particulates on a plurality of electrode pairs positioned inside a common particulate matter (PM) sensor housing of a PM sensor. The method may further include distinguishing size of the distribution of particulates based on a resistance measured independently across each individual electrode pair of the plurality of electrode pairs and further comprising generating a distribution of current across the plurality of electrode pairs based on the resistance across the each individual electrode pair of the plurality of electrode pairs. Herein the method may further include summing the distribution of current of the each individual electrode pair of the plurality of electrode pairs to generate a total current of the PM sensor, determining a total size of the distribution of particulates on the plurality of electrode pairs based on the total current of the PM sensor and responsive to the total current being higher than a threshold, regenerating the PM sensor. The method may further include indicating a leak in a diesel particulate filter positioned upstream of the PM sensor based on a duration between PM sensor regenerations. In another representation of the method, the method may include determining a length of the distribution of particulates on the individual electrode pair based on current across each of the individual electrode pair of the plurality of individual electrodes. As such adjusting engine operation may be further based on the indicating of the leak in the diesel particulate filter and the plurality of electrode pairs may each be electrically isolated from one another and further connected to independent voltage sources and independent measurement devices. The each individual electrode pair may include a first electrode coupled to a positive terminal of a single voltage source and a second electrode coupled to a negative terminal of the single voltage source and wherein the first electrode surrounds the second electrode and is further electrically isolated from the first electrode.

Turning now to FIG. 4, a method 400 for regenerating the PM sensor (such as a PM sensor 106 shown at FIG. 1, for example) is shown. Specifically, when the soot load on the PM sensor is greater than the threshold, or when a resistance of the PM sensor adjusted for temperature drops to a threshold resistance, the PM sensor regeneration conditions may be considered met, and the PM sensor may need to be regenerated to enable further PM detection. At 402, regeneration of the PM sensor may be initiated and the PM sensor may be regenerated by heating up the sensor at 404. The PM sensor may be heated by actuating a heating element coupled thermally to the sensor electrode surface, such as a heating element embedded in the sensor, until the soot load of the sensor has been sufficiently reduced by oxidation of the carbon particles between the electrodes. The PM sensor regeneration is typically controlled by using timers and the timer may be set for a threshold duration at 402. Alternatively, the sensor regeneration may be controlled using a temperature measurement of the sensor tip, or by the control of power to the heater, or any or all of these. When timer is used for PM sensor regeneration, then method 400 includes checking if the threshold duration has elapsed at 406. If the threshold duration has not elapsed, then method 400 proceeds to 408 where the PM sensor regeneration may be continued. If threshold duration has elapsed, then method 400 proceeds to 410 where the PM sensor regeneration may be terminated and the electric circuit may be turned off at 412. Further, the sensor electrodes may be cooled to the exhaust temperature for example. Method 400 proceeds to 414 where the resistance between the electrodes of the PM sensor is measured. From the measured resistance, possibly compensated for temperature, the PM or soot load of the PM sensor (i.e., the accumulated PMs or soot between the electrodes of the PM sensor) may be calculated at 416 and the method proceeds to 418. At 418, the calculated soot load of the PM sensor may be compared with a threshold, Lower_Thr. The threshold Lower_Thr, may be a lower threshold, lower than the regeneration threshold, for example, indicating that the electrodes are sufficiently clean of soot particles. In one example, the threshold may be a threshold below which regeneration may be terminated. If the soot load continues to be greater than Lower_Thr, indicating that further regeneration may be required, method 400 proceeds to 408 where PM sensor regeneration may be repeated. However, if the PM sensor continues to undergo repeated regenerations, the controller may set error codes to indicate that the PM sensor may be degraded or the heating element in the soot sensor may be degraded. If the soot load is lower than the threshold Lower_Thr, indicating that the electrode surface is clean, method 400 proceeds to 420, where the soot sensor resistance and regeneration history may be updated and stored in memory. For example, a frequency of PM sensor regeneration and/or an average duration between sensor regenerations may be updated. At 422, various models may then be used by the controller to calculate the percentage efficiency of the DPF the filtration of soot. In this way, the PM sensor may perform on-board diagnosis of the DPF.

The engine exhaust passage may include one or more PM sensors positioned upstream and/or downstream of the DPF for determining a soot load of the DPF. When the soot sensor is positioned upstream of the DPF, based on the resistance change following soot deposited on the plurality of electrodes of the PM sensor, a soot load on the sensor may be inferred. The soot load thus determined, may be used to update the soot load on the DPF, for example. If the soot load on the DPF is greater than a threshold for DPF regeneration, then the controller may adjust engine operating parameters to regenerate the DPF. Specifically, responsive to filter regeneration conditions being met, a temperature of the filter (or in the vicinity of the filter) may be sufficiently raised to burn off stored soot. This may include operating a heater coupled to the DPF, or raising a temperature of engine exhaust (e.g., by operating rich) flowed into the DPF.

Turning now to FIG. 5, an example method 500 for diagnosing DPF function based on the regeneration time of the PM sensor is shown. At 502, it may be calculated by the controller, through calibration, the time of regeneration for the PM sensor, t(i)_regen, which is the time measured from end of previous regeneration to the start of current regeneration of the PM sensor. At 504, compare t(i)_regen to t(i−1)_regen, which is the previously calibrated time of regeneration of the PM sensor. From this, it may be inferred that the soot sensor may need to cycle through regeneration multiple times in order to diagnose the DPF. If the t(i)_regen is less than half the value of t(i−1) region, then at 508 indicate DPF is leaking, and DPF degradation signal is initiated. Alternatively, or additionally to the process mentioned above, the DPF may be diagnosed using other parameters, such as exhaust temperature, engine speed/load, etc. The degradation signal may be initiated by, for example, a malfunction indication light on diagnostic code. In addition, method 500 includes adjusting engine operation based on indicating leak in the DPF at 510. Adjusting engine operation may include limiting engine torque at 512, for example. In one examples, responsive to detecting leak in the DPF, engine power may be reduced be reduced. Reducing the engine power may reduce the amount of emissions in the exhaust. For example, adjusting engine operation may include adjusting an actuator of a throttle to adjust reduce amount of airflow to an engine thereby reducing torque.

A current regeneration time of less than half of the previous regeneration time may indicate that the time for electric circuit to reach the R regen threshold is shorter, and thus the frequency of regeneration is higher. Higher frequency of regeneration in the PM sensor may indicate that the outflowing exhaust gas is composed of a higher amount of particulate matter than realized with a normally functionally DPF. Thus, if the change of regeneration time in the soot sensor reaches threshold, t_regen, in which the current regeneration time of the PM sensor is less than half of that of the previous regeneration time, a DPF degradation, or leaking, is indicated, for example via a display to an operator, and/or via setting a flag stored in non-transitory memory coupled to the processor, which may be sent to a diagnostic tool coupled to the processor. If the change of regeneration time in the soot sensor does not reach threshold t_regen, then at 506 DPF leaking is not indicated. In this way, leaks in a particulate filter positioned upstream of the particulate matter sensor may be detected based on a rate of deposition of the particulates on the particulate matter sensor element.

Figure 6:
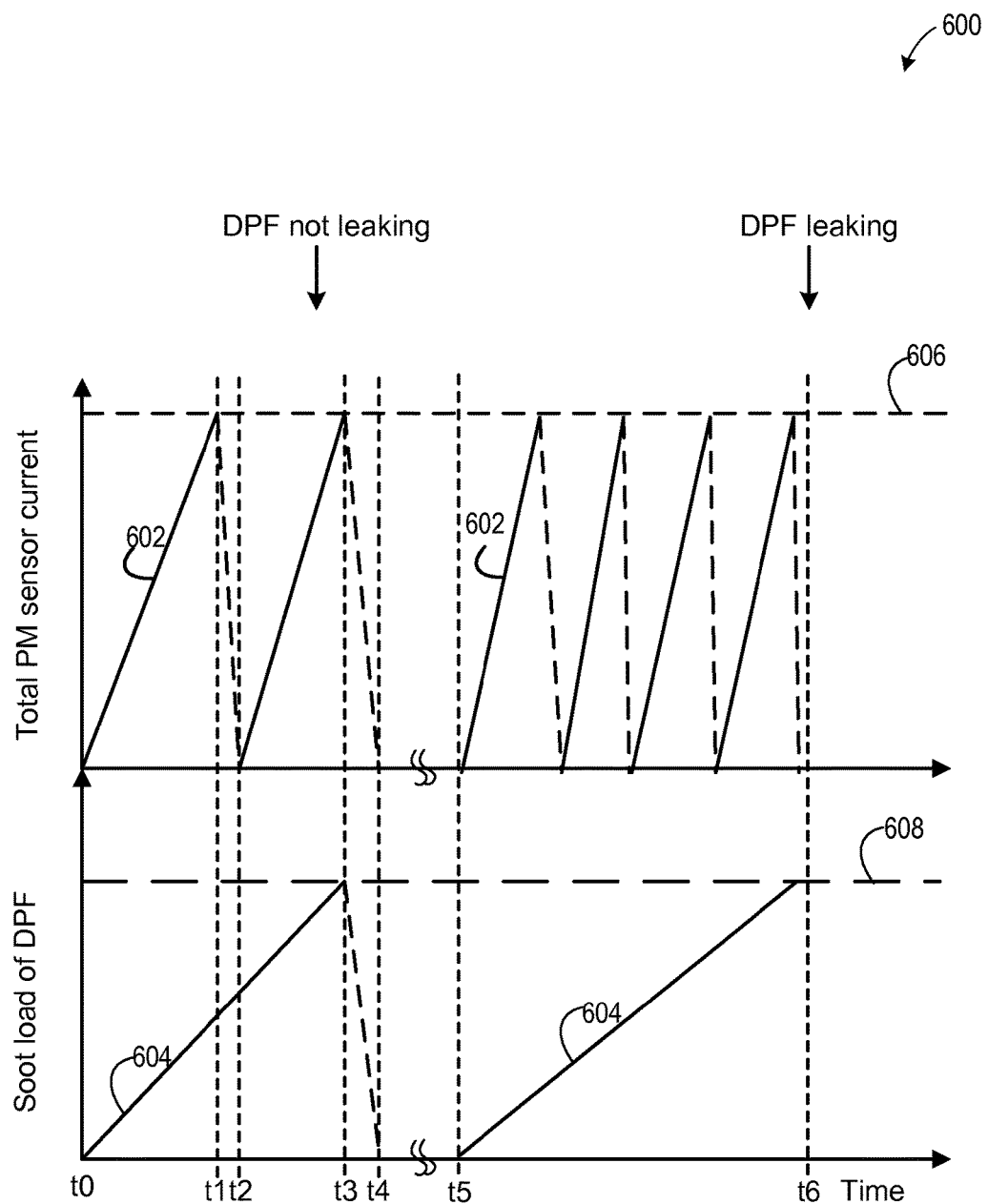
FIG. 6 shows an example relationship between the sum total of current of PM sensor current and soot load on the particulate filter.

Turning now to FIG. 6, map 600 shows an example relationship between the sum total of current of PM sensor current and soot load on the particulate filter. Specifically, map 600 shows a graphical depiction of the relationship between PM sensor regeneration and the soot load of the DPF, specifically how PM sensor regeneration may indicate DPF degradation. Vertical markers t0, t1, t2, t3, t4, t5 and t6 identify significant times in the operation and system of PM sensor and particulate filter.

The first plot from the top of FIG. 6 shows total PM sensor current of the PM sensor. As previously described, when PMs get deposited across individual electrode pairs of the plurality of electrode pairs of the PM sensor, the current measured across the individual electrode pairs may begin to increase, and the sum total of the currents measured across the plurality of individual electrode pairs may be determined as the total PM sensor current (plot 602) of the PM sensor. As such, the total PM sensor current is at its lowest value at the bottom of the plot and increases in magnitude toward the top of the plot in the vertical direction. The horizontal direction represents time and time increases from the left to the right side of the plot. Horizontal marker 606 represents the threshold current for regeneration of the PM sensor in the top plot. Plot 604 represents the soot load on the DPF, and the horizontal marker 608 represents the threshold soot load of DPF in the second plot.

Between t0 and t1, a PM sensor regeneration cycle is shown. At time t0, the PM sensor is in a relatively clean condition, as measured by low total PM sensor current. When a controller coupled to the PM sensor determines the total PM sensor current by summing the current across the plurality of measurement devices, and further determines the current to be small, it may send instructions to a regeneration circuit to end supplying heat, so that a detection circuit may begin detecting PM load accumulation. As PM load increases on the sensor, the total PM sensor current begins to increase (602). Between t0 and t1, PM continues to accumulate and the total PM sensor current (plot 602) increases accordingly and further soot load on DPF also increases (plot 604). In some examples, soot load on the DPF may be based on PM sensor load when PM sensor is located upstream of DPF, for example. The controller may be able to calculate distribution of PM and further determine size of PM present in PM sensor by calculating the change in current, for example. As such, based on the size of the PM, currents across one or more of the measurement devices may saturate, for example.

At t1, the PM sensor current (plot 602) reaches the threshold current for regeneration of the PM sensor (marker 606). At t1, PM sensor regeneration may be initiated as explained earlier. Thus, between t1 and t2, the PM sensor may be regenerated by turning on electric circuit for regeneration, for example. At t2, the PM sensor may be sufficiently cool, and may begin to accumulate PMs. Thus, between t2 and t3 (DPF regeneration cycle), the PM sensor may continue to accumulate PMs. During time between t2 and t3, DPF soot load continues to increase (plot 604). However, at t3, the soot load on the DPF (plot 604) reaches the threshold soot load for DPF regeneration (marker 608). Between t3 and t4, the DPF may be regenerated to burn off the soot deposited on the DPF as explained earlier. Further at t4, the PM sensor regeneration frequency may be compared with previous regeneration frequency of the PM sensor. Based on the PM sensor regeneration frequency remaining similar to previous cycles, the DPF maybe determined to be not leaking. In this way, based on PM sensor output, DPF may be monitored and diagnosed for leaks.

Between t5 and t6, another DPF cycle is shown. Herein, between t5 and t6, the soot load on the DPF gradually increases (plot 604). During this time, the total PM sensor current may be monitored. Plot 602 shows the PM sensor going through multiple regeneration cycles as described earlier. However, the frequency of regeneration of the PM sensor has nearly doubled (plot 602). As explained earlier, higher frequency of regeneration in the PM sensor may indicate that the outflowing exhaust gas is composed of a higher amount of particulate matter than realized with a normally functionally DPF, therefore at t6, DPF leak may be indicated.

In this way, a more accurate measure of the exhaust PM load, and thereby the DPF soot load can be determined. As such, this improves the efficiency of filter regeneration operations, and reduces the need for extensive algorithms. In addition, by enabling more accurate diagnosis of an exhaust DPF, exhaust emissions compliance may be improved. As such, this reduces the high warranty costs of replacing functional particulate filters and exhaust emissions are improved and exhaust component life is extended. Furthermore, by using plurality of individual electrodes connected to plurality of measurement devices and plurality of voltage sources, an accurate measure of the PM sensor loading may be determined. By summing the current across multiple individual electrode pairs, PM sensor may detect PMs in the exhaust more accurately, and not be affected by large particulates depositing on the electrodes, for example. The technical effect of summing the currents generated across multiple individual electrode pairs is that the PM sensor may detect PMs exiting the DPF more accurately, and hence diagnose the DPF for leaks in a more reliable fashion.

The systems and methods described above also provide for a method of particulate matter sensing, the method including adjusting engine operation responsive to a distribution of particulates on a plurality of electrode pairs positioned inside a common particulate matter (PM) sensor housing of a PM sensor. In a first example of the method, the method may additionally or alternatively include distinguishing size of the distribution of particulates based on a resistance measured independently across each individual electrode pair of the plurality of electrode pairs and further comprising generating a distribution of current across the plurality of electrode pairs based on the resistance across the each individual electrode pair of the plurality of electrode pairs. A second example of the method optionally includes the first example and further includes summing the distribution of current of the each individual electrode pair of the plurality of electrode pairs to generate a total current of the PM sensor, determining a total size of the distribution of particulates on the plurality of electrode pairs based on the total current of the PM sensor; and responsive to the total current being higher than a threshold, regenerating the PM sensor. A third example of the method optionally includes one or more of the first and second examples, and further includes indicating a leak in a diesel particulate filter positioned upstream of the PM sensor based on a duration between PM sensor regenerations. A fourth example of the method optionally includes one or more of the first through third examples, and further includes wherein the adjusting engine operation is further based on the indicating of the leak in the diesel particulate filter. A fifth example of the method optionally includes one or more of the first through fourth examples, and further includes wherein the plurality of electrode pairs are each electrically isolated from one another and further connected to independent voltage sources and independent measurement devices. A sixth example of the method optionally includes one or more of the first through fifth examples, and further includes wherein the each individual electrode pair includes a first electrode coupled to a positive terminal of a single voltage source and a second electrode coupled to a negative terminal of the single voltage source and wherein the first electrode surrounds the second electrode and is further electrically isolated from the first electrode.

The systems and methods described above also provide for a method of particulate matter sensing, in a particulate matter sensor system, the method, comprising accumulating particulate matter (PM) in an engine exhaust across each individual electrode pair of a plurality of electrode pairs located inside a PM sensor, independently generating a current across the each individual electrode pair responsive to accumulated particulate matter, distinguishing particulate matter size based on the current, and summing the current across a plurality of electrode pairs to generate a total current of the PM sensor. In a first example of the method, the method may additionally or alternatively include wherein the total current increases proportion to the particulate matter size. A second example of the method optionally includes the first example, and further includes regenerating the PM sensor when the total current of the PM sensor is greater than a threshold current. A third example of the method optionally includes one or more of the first and the second examples, and further includes indicating a leak in a particulate filter positioned upstream of the PM sensor when a duration between regenerations of the PM sensor is lower than a threshold. A fourth example of the method optionally includes one or more of the first through the third examples, and further includes not indicating the leak in the particulate filter when the duration between regenerations of the PM sensor is greater than the threshold. A fifth example of the method optionally includes one or more of the first through the fourth examples, and further includes wherein each individual electrode pair of the plurality of electrode pairs includes a positive pad connected to a positive terminal of a voltage source and a negative pad connected to a negative terminal of the voltage source, the positive pad surrounding the negative pad and further separated by a distance.

The systems and methods described above also provide for a particulate matter (PM) sensor system comprising a PM sensor including a plurality of planar interdigitated electrode pairs and plurality of voltage sources wherein each individual planar interdigitated electrode pair of the plurality of interdigitated electrode pairs includes a positive electrode and a negative electrode, the positive electrode electrically coupled to a positive terminal of a voltage source via a measurement device, the negative electrode electrically coupled to a negative terminal of the voltage source, the each individual electrode pair isolated from one another by an insulating gap. In a first example of the particulate matter sensor system, the sensor may additionally or alternatively include wherein the negative electrode of each individual planar interdigitated electrode pair comprises a first electrode wire extending a first distance along a first direction and a second electrode wire extending a second distance along a second direction, the first direction is orthogonal to the second direction, and the second distance is greater than the first distance. A second example of the particulate matter sensor system optionally includes the first example and further includes wherein the first electrode wire of the negative electrode is electrically coupled to the second electrical wire forming a junction between the first electrode wire and the second electrode wire, and further electrically coupled to the negative terminal of the voltage source. A third example of the particulate matter sensor system optionally includes one or more of the first and the second examples, and further includes wherein the positive electrode of each of the individual planar interdigitated electrode pair comprises a positive electrode wire adjacent to each of the first electrode wire and the second electrode wire enveloping the second electrode wire of the negative electrode and further isolated from each of the first electrode wire and the second electrode wire of the first negative electrode and further connected to the positive terminal of the voltage source. A fourth example of the particulate matter sensor system optionally includes one or more of the first through the third examples, and further includes a controller with computer readable instructions stored on non-transitory memory for accumulating PMs across each of the positive electrode and the negative electrode of the individual planar interdigitated electrode pair by accumulating the PM between one or more of first electrode wire, the second electrode wire, and the positive electrode wire. A fifth example of the particulate matter sensor system optionally includes one or more of the first through the fourth examples, and further includes wherein the PM sensor is positioned downstream of a particulate filter in an engine exhaust passage, and wherein the controller includes further instructions for generating a current across each of the individual planar interdigitated electrode pair, summing the current generated across each of the individual planar interdigitated electrode pair and generating a total current of the PM sensor, and regenerating the PM sensor when the total current is higher than a threshold. A sixth example of the particulate matter sensor system optionally includes one or more of the first through the fifth examples, and further includes wherein the controller includes further instructions for indicating leak in the particulate filter based on a duration between regenerations of the PM sensor.

Note that the example control and estimation routines included herein can be used with various engine and/or vehicle system configurations. The control methods and routines disclosed herein may be stored as executable instructions in non-transitory memory and may be carried out by the control system including the controller in combination with the various sensors, actuators, and other engine hardware. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated actions, operations and/or functions may be repeatedly performed depending on the particular strategy being used. Further, the described actions, operations and/or functions may graphically represent code to be programmed into non-transitory memory of the computer readable storage medium in the engine control system, where the described actions are carried out by executing the instructions in a system including the various engine hardware components in combination with the electronic controller.

It will be appreciated that the configurations and routines disclosed herein are exemplary in nature, and that these specific embodiments are not to be considered in a limiting sense, because numerous variations are possible. For example, the above technology can be applied to V-6, I-4, I-6, V-12, opposed 4, and other engine types. The subject matter of the present disclosure includes all novel and non-obvious combinations and sub-combinations of the various systems and configurations, and other features, functions, and/or properties disclosed herein.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. A method, comprising:
adjusting engine operation responsive to a distribution of particulates on a plurality of electrode pairs positioned inside a common particulate matter (PM) sensor housing of a PM sensor; and
distinguishing a size of the distribution of particulates based on a resistance measured independently across each individual electrode pair of the plurality of electrode pairs, and further comprising generating a distribution of current across the plurality of electrode pairs based on the resistance across each individual electrode pair of the plurality of electrode pairs.

2. The method of claim 1, further comprising:
summing the distribution of current of each individual electrode pair of the plurality of electrode pairs to generate a total current of the PM sensor;
determining a total size of the distribution of particulates on the plurality of electrode pairs based on the total current of the PM sensor; and
responsive to the total current being higher than a threshold, regenerating the PM sensor.

3. The method of claim 2, further comprising indicating a leak in a diesel particulate filter positioned upstream of the PM sensor based on a duration between PM sensor regenerations.

4. The method of claim 3, wherein the adjusting engine operation is further based on the indicating of the leak in the diesel particulate filter.

5. The method of claim 1, wherein the plurality of electrode pairs is each electrically isolated from one another and further connected to independent voltage sources and independent measurement devices.

6. The method of claim 5, wherein each individual electrode pair includes a first electrode coupled to a positive terminal of a single voltage source and a second electrode coupled to a negative terminal of the single voltage source and wherein the first electrode surrounds the second electrode and is further electrically isolated from the first electrode.

7. A method, comprising:
accumulating particulate matter (PM) in an engine exhaust across each individual electrode pair of a plurality of electrode pairs located inside a PM sensor;
independently generating a current across each individual electrode pair responsive to the accumulated PM;
distinguishing PM size based on the current; and
summing the current across each of the individual electrode pairs of the plurality of electrode pairs to generate a total current of the PM sensor.

8. The method of claim 7, wherein the total current increases proportionally to the PM size.

9. The method of claim 8, further comprising regenerating the PM sensor when the total current of the PM sensor is greater than a threshold current.

10. The method of claim 9, further comprising indicating a leak in a particulate filter positioned upstream of the PM sensor when a duration between regenerations of the PM sensor is lower than a threshold.

11. The method of claim 10, further comprising not indicating the leak in the particulate filter when the duration between regenerations of the PM sensor is greater than the threshold.

12. The method of claim 7, wherein each individual electrode pair of the plurality of electrode pairs includes a positive pad connected to a positive terminal of a voltage source and a negative pad connected to a negative terminal of the voltage source, the positive pad surrounding the negative pad and further separated by a distance.

\* \* \* \* \*